(12) United States Patent
Richter et al.

(10) Patent No.: US 10,241,104 B2
(45) Date of Patent: Mar. 26, 2019

(54) SYSTEM FOR INTERACTING WITH A CELL

(71) Applicants: Wolfgang Richter, Vancouver (CA); Faranak Zadeh, Vancouver (CA)

(72) Inventors: Wolfgang Richter, Vancouver (CA); Faranak Zadeh, Vancouver (CA)

(73) Assignee: EPIC SEMICONDUCTORS INC., Vancouver, British Columbia (CA)

( * ) Notice: Subject to any disclaimer, the term of this patent is extended or adjusted under 35 U.S.C. 154(b) by 229 days.

(21) Appl. No.: 15/258,568

(22) Filed: Sep. 7, 2016

(65) Prior Publication Data

US 2018/0067100 A1    Mar. 8, 2018

(51) Int. Cl.
*A61N 1/02* (2006.01)
*A61B 5/053* (2006.01)
(Continued)

(52) U.S. Cl.
CPC ..... *G01N 33/48728* (2013.01); *A61B 5/0538* (2013.01); *A61B 5/4836* (2013.01);
(Continued)

(58) Field of Classification Search
CPC .............. G01N 33/48728; G01N 27/60; A61B 5/0538; A61N 1/025; A61N 1/40
See application file for complete search history.

(56) References Cited

U.S. PATENT DOCUMENTS

2004/0182707 A1*  9/2004 Jardemark et al.
2007/0155016 A1*  7/2007 Lee et al.
(Continued)

Primary Examiner — Matthew F Desanto

(57) ABSTRACT

Disclosed is a system for interacting with a cell and further communicating over a communication network is provided. The system includes a controller, a frequency generator, a first electrode, and a cell-chip circuitry. The frequency generator provides modulated alternating electric field with variable frequency. The controller releases routing instructions and further communicates through the communication network. The first electrode receives alternating electric field charges from the controller. The cell-chip circuitry is capacitively coupled to the first electrode. The cell-chip circuitry includes a second electrode, a harvester, a processor, a pulser, an analog switch matrix, a bi-directional communication unit, a pit, an inherent artificial intelligence interpreter, a analyzer, a nano needle, a third electrode. The cell-chip circuitry measures the field strength of the received charges from the harvester and generates pulsed intervals depending upon the field strength. The cell-chip circuitry further measures and communicates data with the controller through the e-field. The pit receives the cell. The cell reacts to the e-field. The inherent artificial intelligence interpreter performs successive approximation to monitor the reaction on the cell inside the pit on receiving instructions from the controller. The analyzer measures analog values of the e-field on the cell under the command of the inherent artificial intelligence interpreter; the analyzer communicates data to the bi-directional communication unit. The nano needle is inserted in the pit for bi-directionally communicating the e-field on the cell, and the third electrode is configured to provide space for the pit and floats against the ground.

14 Claims, 3 Drawing Sheets

(51) Int. Cl.
*G01N 33/487* (2006.01)
*G01N 27/06* (2006.01)
*G01N 27/60* (2006.01)
*A61N 1/40* (2006.01)
*A61N 1/372* (2006.01)
*A61B 5/00* (2006.01)
*H04L 29/08* (2006.01)

(52) U.S. Cl.
CPC ......... *A61N 1/025* (2013.01); *A61N 1/37282* (2013.01); *A61N 1/40* (2013.01); *G01N 27/60* (2013.01); *H04L 67/10* (2013.01)

(56) References Cited

U.S. PATENT DOCUMENTS

2012/0004523 A1* 1/2012 Richter et al.
2013/0206720 A1* 8/2013 Blom et al.
2016/0199853 A1* 7/2016 Harwood et al.

* cited by examiner

SYSTEM FOR INTERACTING WITH A CELL

BACKGROUND OF THE INVENTION

1. Field of the Invention

The present invention generally relates to a system for interacting with a cell, and more particularly relates to a system for manipulating the electrical potential and field effects of molecules or cells.

2. Description of Related Art

Cancer is one of the major causes of hospitalization and death worldwide. Many of the therapies applied to cancer treatment are either ineffective or not well-tolerated by the patient. A promising approach that is little known but which has been successfully applied in Sweden, China, Germany, and Japan involves the electrical stimulation of a malignant tumor using direct current electricity.

Many scientists today are researching on treatment of cancer or other cell-borne diseases. Drugs and radiation therapy are conventional approaches to treat cancer. The scientists study electron bindings, ionization, or (bio-) chemical reactions, with means of visual microscopic inspection and tests of electric cell potential.

Heisenberg postulated "we alter what we watch", which means that monitoring of an object may change the behavior of the object and gives false information that leads to wrong interpretation. This may be a reason that existing methods of research don't work properly. Therefore, there is a need of a system that avoid overwhelming alterations or to learn from occurring alterations that can be monitored during an examination process of molecules or cells.

Light, electron or scanning tunneling (STM) microscopes are known and used in the scientific world to watch even the tiniest particles of cells and even structures on an atomic level. Further, various scientific apparatus are known to create magnetic or electric fields to manipulate behavior of organic matter.

The lab-on-chip or printed-lab-on-polymer-foils present to the scientific world are mostly used for analytical research. Software algorithms are apparently used in supercomputers that try to simulate cell behavior. Further, various test strips are known to check body liquids like blood or urine. These strips use markers which change the colors in a kind of chemical reaction which indicates a state of health.

These studies not only can tell how different matter interacts with each other but also lead to methods to force or prevent such effects. Researcher's worldwide quest and study since decades with no cure in sight, cancer, HIV, malaria and other epidemic plagues claim countless lives every day.

Experiment methods are purposely examined on test animals which help in predicting possible human reactions to same medicine under the same conditions, and further can be used as reference to clinical experiment imitation. However, these are the tests of trial and error. Most of these tests do not work. Further, such tests are costly, long lasting and also cost the life of millions of innocent animals used as research objects. So, a need has arisen to create a new system that removes the need to test on animals.

Therefore, there is a need of a system for interacting (analyzing and measuring) with a cell (organic cell) under the influence of electric field and communicates over a communication network. Further, the system should be able to manipulate the cell inside the living organism. Further, the system should be able to treat cell based diseases inside the living organism using the electric field.

SUMMARY OF THE INVENTION

In accordance with teachings of the present invention, a system for interacting with a cell and further communicating over a communication network is provided.

An object of the present invention is to provide the system with a frequency generator, a controller, a first electrode, and a cell-chip circuitry. The frequency generator provides modulated alternating electric field with variable frequency. The controller releases routing instructions and further communicates through the communication network.

The first electrode receives alternating electric field charges (hereinafter refer to as e-field) from the controller. The cell-chip circuitry is capacitvely coupled to the first electrode. The cell-chip circuitry includes a second electrode, a harvester, a processor, a pulser, an analog digital switch matrix, a bi-directional communication unit, a pit, an inherent artificial intelligence interpreter, a analyzer, a nano needle, a third electrode.

The second electrode mirrors alternating charges and further couples to the first electrode. The harvester converts the alternating electric field into DC power and further extracts clock signals synchronized with the e-field frequency. The processor processes external operation commands and data received from the controller.

The pulser measures the field strength of the received charges from the harvester and generates pulsed intervals depending upon the field strength. The analog digital switch matrix receives routing instructions from the controller for making conditional temporary connections under the control of the processor, further the analog switch matrix routes pulsed intervals.

The bi-directional communication unit modulates commands and bi-directionally communicates data with the controller through the e-field. The pit receives the cell. The cell reacts to the e-field. The inherent artificial intelligence interpreter performs successive approximation to monitor the reaction on the cell inside the pit on receiving instructions from the controller.

The analyzer measures analog values of the e-field on the cell under the command of the inherent artificial intelligence interpreter, the analyzer communicates data to the bi-directional communication unit. The nano needle is inserted in the pit for bi-directionally communicating the e-field on the cell, and the third electrode is configured to provide space for the pit and floats against the ground.

In another aspect of the invention, the cell-chip circuitry further includes a charge chamber for switching polarized charges into the pit to ionize the cell. Further, the nanoneedle is movable inside the pit towards the cell. Furthermore, the nano needle inside the pit communicates charges on the cell surface. The nano needle is smaller in size than of the cell.

In another aspect of the invention, the second electrode couples capacitively to the controller to get energy, clock, data from mirrored alternating charges. Further, the cell-chip circuitry is inserted in living organisms to examine the cell. Furthermore, the charge chamber ionizes the cell to prevent the collagen for creating fiber towards a cancer cell inside the living organisms.

In yet another aspect of the invention, each of the one or more cell-chip circuitries are connected via charge coupling. Further, the analog value is converted to digital value by the inherent artificial intelligence interpreter. Furthermore, the pulsed intervals are routed to the sub-circuits of the cell-chip circuitry.

These and other features and advantages will become apparent from the following detailed description of illustrative embodiments thereof, which is to be read in connection with the accompanying drawings.

Figure 1:
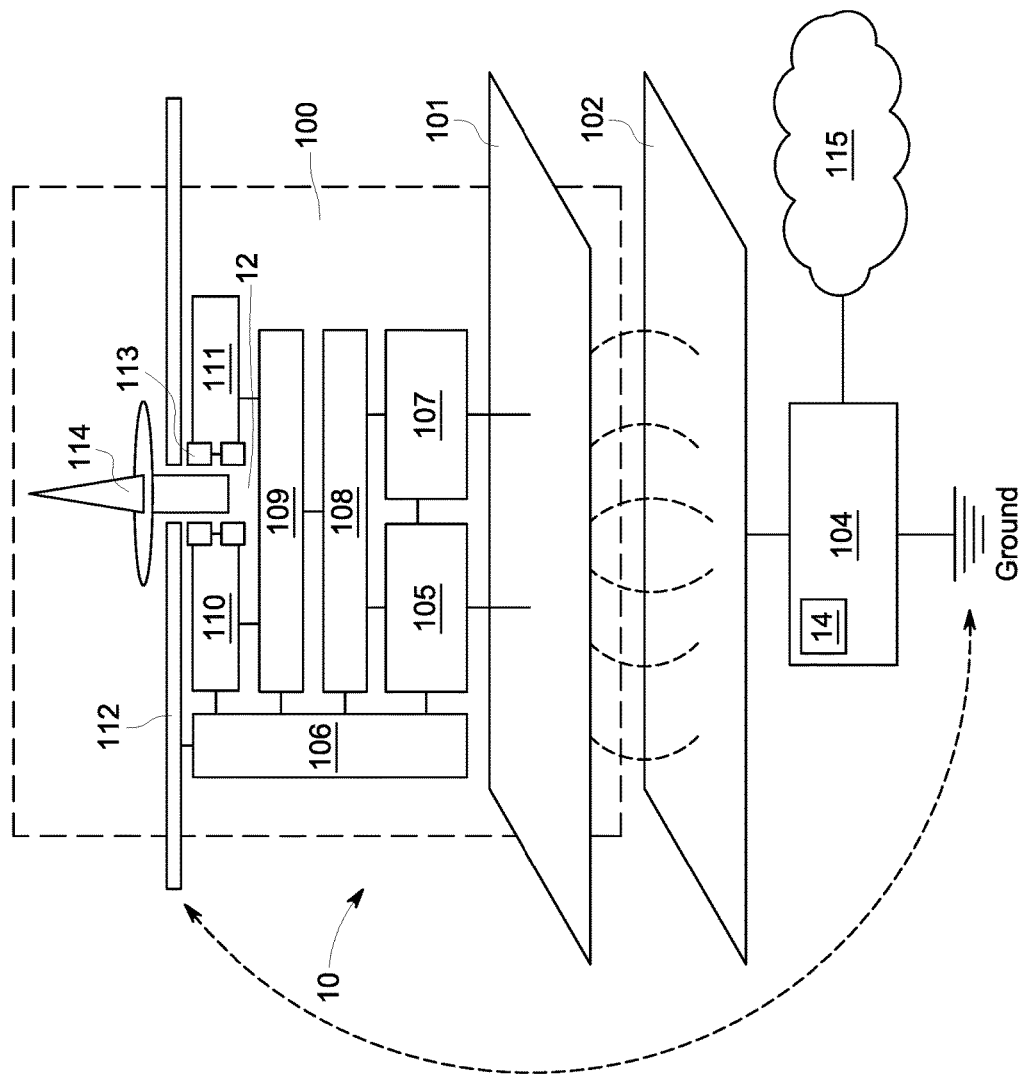
FIG. 1 illustrates a block diagram of a system for interacting with a cell in a preferred embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF DRAWINGS

While this technology is illustrated and described in a preferred embodiment of a system for interacting with a cell that may be produced in many different configurations, forms and materials. There is depicted in the drawings, and will herein be described in detail, as a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the technology described herein.

Reference will now be made in detail to several embodiments of the invention which are illustrated in the accompanying drawings. Wherever feasible and convenient, the same reference numerals are used in the figures and the description to refer to the same or like parts. The drawings are in a simplified form and not to precise scale. For purposes of convenience and clarity only, directional terms, such as top, bottom, left, right, up, down, over, above, below, beneath, rear, and front may be used with respect to the accompanying drawings.

These and similar directional terms should not be strictly construed to limit the scope of the invention. In addition, words such as attached, affixed, coupled, connected and similar terms with their inflectional morphemes are used interchangeably, unless the difference is noted or made otherwise clear from the context. These words and expressions do not necessarily signify direct connections, but include connections through mediate components and devices.

FIG. 1 illustrates a block diagram of a system 10 for interacting with a cell in a preferred embodiment of the present invention. The system 10 further communicates over a communication network 115. The system 10 includes a controller 104, a first electrode 102, and a cell-chip circuitry 100. The controller 104 provides modulated alternating electric field with variable frequency. The controller 104 releases routing instructions.

Examples of the controller 104 include but not limited to microcontroller, system on chip (SOC), FPGA, state machines etc. The controller 104 includes a frequency generator 14 to generate variable frequency. Example of the frequency generator 14 includes but not limited to oscillator, resonator, PWM etc.

The controller 104 communicates through the communication network 115. In a preferred embodiment of the present invention, the communication network 115 is internet. However, it would be readily apparent to those skilled in the art may envision various communication network 115 without deviating from the scope of the present invention.

The first electrode 102 receives alternating electric field charges from the controller 104. The cell-chip circuitry 100 is capacitively coupled to the first electrode 102. The cell-chip circuitry 100 includes a second electrode 101, a harvester 105, a processor 108, a pulser 111, an analog digital switch matrix 106, a bi-directional communication unit 107, a pit 12, an inherent artificial intelligence interpreter 109, a analyzer 110, a nano needle 114, and a third electrode 112.

The second electrode 101 mirrors alternating charges and further couples to the first electrode 102. The harvester 105 converts the alternating electric field into DC power and further extracts clock signals synchronized with the e-field frequency. The processor 108 processes external operation commands and data received from the controller 104.

Examples of the harvester 105 include but not limited to rectifier, Graetz bridge, AC-DC convertor, MOS switches etc. Examples of the processor 108 includes but not limited to gate logic, shift registers, comparators, state machines etc. The pulser 111 measures the field strength of the received charges from the harvester 105 and generates pulsed intervals depending upon the field strength. Example of the pulser 111 includes but not limited to voltage controlled pulse oscillator (VCP), VCO etc.

The analog digital switch matrix 106 receives routing instructions from the controller 104 for making conditional temporary connections under the control of the processor 108. Further, the analog digital switch matrix 106 routes pulsed intervals. Examples of the analog digital switch matrix 106 include but not limited to transistors, tri-state gates, MEMS switches etc.

The bi-directional communication unit 107 modulates commands and bi-directionally communicates data with the controller 104 through the e-field. Examples of the bi-directional communication unit 107 includes but not limited to AM or FM (de) modulators, modem sub-circuits, peak detectors, side-band modulators etc.

The pit 12 is like a hole configured through the third electrode 112 to receive the cell. The cell reacts to the e-field. The pit 12 may be configured through third electrode 112 in various shapes, sizes and configuration. The size of the pit 112 is in range of 3 to 6 micro-meter. The walls of pit 112 are insulated by using materials like silicon dioxide.

When, the cell is inside the pit 112, they have no direct contact to the sub-circuits of the cell-chip circuitry 100. The cell inside the pit 112 is seen as dialectic with impedance changing at certain frequencies. The process of measuring impedance or resonance is similar to e-field tomography.

The inherent artificial intelligence interpreter 109 performs successive approximation to monitor the reaction on the cell inside the pit 12 on receiving instructions from the controller 104. Examples of the inherent artificial intelligence interpreter 109 includes but not limited to shift registers, logic gates, conditional logic elements, comparators etc.

The analyzer 110 measures analog values of the e-field on the cell under the command of the inherent artificial intelligence interpreter 109. The analyzer 110 communicates data to the bi-directional communication unit 107. Example of the analyzer 110 includes but not limited to instrumentations amplifiers (INA), operational amplifiers (OPA), auto-gain stages, analog comparators, comb filters etc.

The nano needle 114 is inserted in the pit 12 for bi-directionally communicating the e-field on the cell. The third electrode 112 is configured to provide space for the pit 12 and floats against the ground. Example of the nano needle 114 includes but not limited to carbon tubes, nano silver etc. The nano needle 114 extends the charges form the sub-circuits of cell-chip circuitry 100 as small as a single field line towards a specimen or sample.

The third electrode 112 provides electrostatic shields to the pit 12. The third electrode 112 contains a hole that provides an opening to the pit 12 for intake of the cell or the nano needle 114. In another preferred embodiment of the present invention, the pit 12 is able to receive markers or medicines or other substances required for reference.

In another preferred embodiment of the present invention, the nano needle 114 penetrates the semi-conductive material of cell-chip circuitry 100. It passes layers which may have different positive and negative conductive zones, like a wall made of tiny bricks. In the present invention, such bricks of the cellchip circuitry 10 are polarized switches or diodes with adjustable impedance. The system 10 thus sends details of the electric potential on the cell inside the pit 12. The information then helps the user know about the condition of the cell.

In another preferred embodiment of the present invention, the cell-chip circuitry 100 includes a charge chamber 113 for switching polarized charges into the pit 12 to ionize the cell. Examples of charge chamber 113 include but not limited to CMOS switches, diodes, MEMS switches, Optocouplers etc.

The user is able to remotely manipulate the potential on the cell using the charge chamber 113. For exemplary purposes, a cancerous cell has a charge potential of 5 V and a normal cell has charge potential of 2V. Thus, every cell-based disease may be treated by using the charge chamber 113. The charge chamber 113 receives signal from the inherent artificial intelligence interpreter 109 to determine the amount of charge potential required to be switched on the cell.

Example of cell-based diseases includes but not limited to cancer, HIV, Diabetes, infections, Alzheimer, hearing and visual impairments bacteria, malaria, fungus, Ebola, Zika etc.

Figure 2:
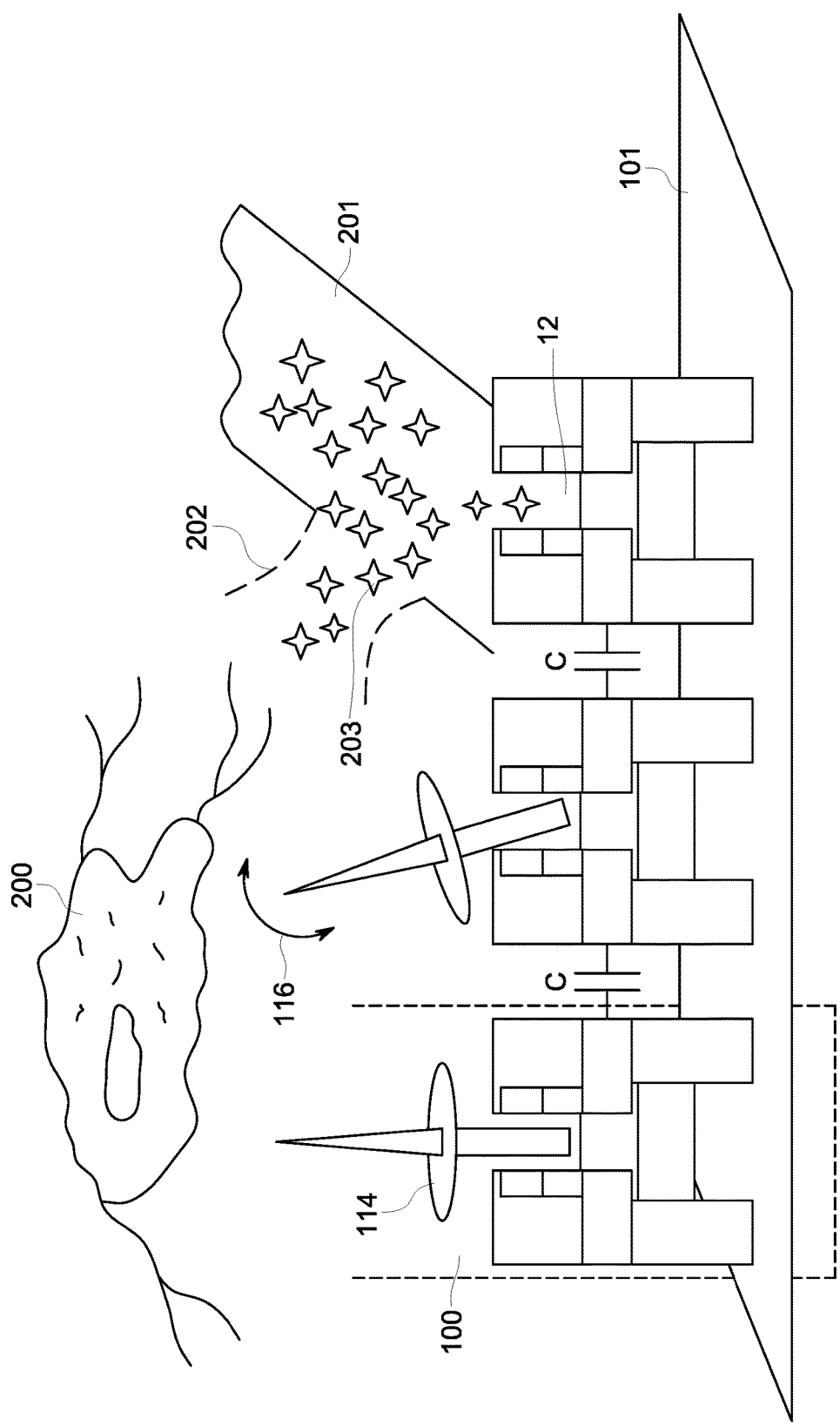
FIG. 2 illustrates an exemplary embodiment of an array of system used for measuring and manipulating potential on the cell.

FIG. 2 illustrates an exemplary embodiment of an array of system 10 used for measuring and manipulating potential on the cell 200. In preferred embodiment of the present invention, the cell-chip circuitry 100 are capacitively coupled (C) to each other or by building a huge shift register to read out or be loaded to/and from the controller (not shown in FIG. 2). Herein the cell 200 is a cancer cell 200.

As shown in FIG. 2, the cancer cell 200 influences a vessel 201 containing collagen 203 by applying charges presumptly of ionized energy. The vessel 201 mirrors the charges from the cancer cell 200 and create an equal charge potential in the vessel's surface 202. The cancer cell 200 splits at point 202 of a vessel 201.

The cancer cell 200 further causes collagen 203 to grow fibers in its direction. The process of attraction of collagen 203 by the cancer cell 200 is known as 'Waterfall' or 'Avalanche' effect, where tumor cell penetrates material and influences organic tissue of a host which becomes sick. Tumors, bacteria, and viruses have their special strategies to harm the living organisms.

The array of cell-chip circuitry 100 detects the ionization or other bio-chemical or bio-electrical effects on the cell caused due to such intrusions or infestations. The nano needle 114 moves inside the pit towards the cell. The nano needle 114 moves to and fro as shown by arrow 116. In an exemplary embodiment of FIG. 2, the nano needle 114 communicates charges on the cell surface. The nano needle 114 may also vibrate to rip off the cell surface or kill bacteria or other micro-organisms.

The nano needle 114 intrudes the cell like a medical searcher, probe or spear. The nano needle 114 may be shoot-out into the cancer cell 200. The plurality of such needles 114 may be pre-charged and applied to the cell-chip circuitry 100, attracted by a counter charge with opposite polarity emitted from the pit 12.

The nano needle 114 may be swallowed or injected in the living organism. The nano needle 114 reaches to the pit 12 of the system 10 because of the ionization. Once, the analyzer measures the cancer cell, the nano needle 114 is propelled from the pit 12 to penetrate the cancer cell, then another nano needle takes its place in the pit 12.

In an exemplary embodiment, the collagen 203 may also be stored temporarily in one or more pits 12 to check its electrically state conditions or alterations under the influence of cancer cell 200. Further in another exemplary embodiment, the molecule of gases may also enter in the pit 12 to get detected and analyzed by the sub-circuits of the cell-chip circuitry 100.

Further in another preferred embodiment of the present, the system 10 includes capillary tubes to lead samples (cell, micro-organisms etc) to the pit 12. The capillary tubes may be used for lab-on-chip solutions.

Figure 3:
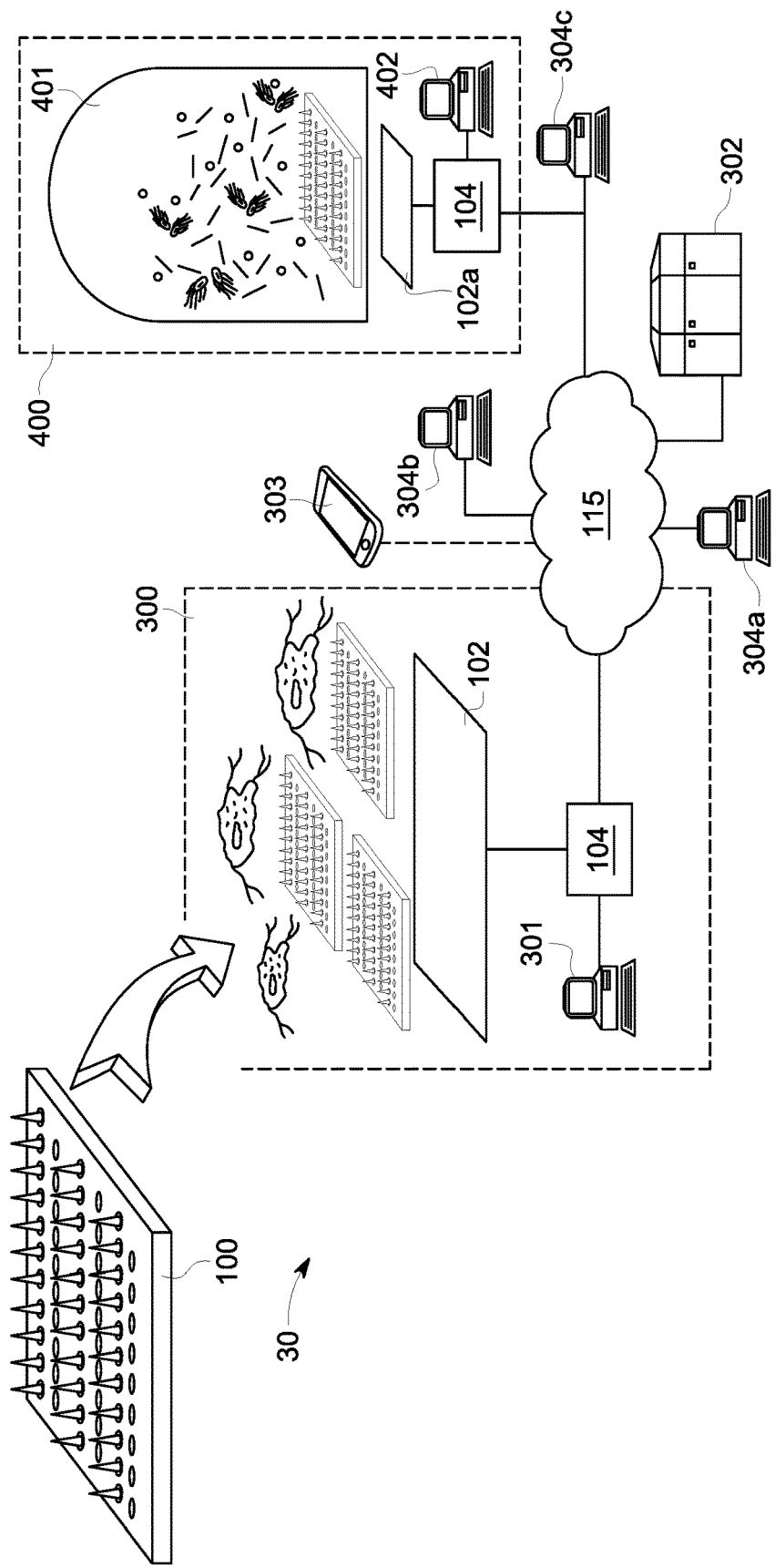
FIG. 3 illustrates another exemplary embodiment of a system representing a bio-chemical analyzing system.

FIG. 3 illustrates another exemplary embodiment of a system 30 representing a bio-chemical analyzing system. The system 30 includes an array of cell-chip circuitry 100 communicating with cell-chip circuitry 300 under the influence of e-field emitted from the electrode 102. The cell-chip circuitry 300 contains plurality of arrays of cell-chip circuitry 100 formed in array and is placed inside the living organism.

The cell-chip circuitry 300 communicates with the controller 104. The controller 104 further communicates data over the communication network 115. The controller 104 may further be connected to local computers 301. Further, the data is communicated to super computers 302, smart phones 303, tables etc via the communication network 115.

The local computers 301, super computers 302, smart phones 303 either alone or in combination with databases or data centers, may have access to data or contribute topics or measurement results. For example, blood sugar etc, to complete the knowledge of the system. Further, the work stations 304a, 304b and 304c of a research institute/universities may be also be connected via the communication network 115.

Further, the system 30 may communicate to a remote location 400 via the communication network 115. For exemplary purposes, the remote location 400 is examining particles, germs, molecules, liquids or gases in a chamber 401.

The chamber 401 is filled with air, gases, liquids, or creates environment in different pressures, temperatures or a vacuum.

Further, as shown in FIG. 3, the controller 104 is emitting energy and data via alternating charges over its own electrode 102a. The system 30 is independently controlled by at least one work station 402 or may also controlled by other external devices communicating over the communication network 115.

The results of other measurement devices specially bioreactors or personal wellness or health analyzing may be used to influence the research results of the CellChip arrays. In principle 401 could also be a product package or container with a product inside which needs to be monitored, for example, food or medicaments which decay over time or get influenced by micro organisms.

The present invention may be used for various applications such as medical devices, clothes, packages, tools etc. Further, the present invention may be used in undergarments like Bra, Panties, and Diapers etc. Furthermore in the present invention, may prevent or fight diseases like diabetics, cancer, malaria, Alzheimer, bacterium, fungus or viruses. Furthermore, the present invention is used to test the quality of the food or water, or as food implants to monitor digestive processes, manipulate organ functions, inside or outside living beings (cow, chicken, other livestock etc).

Furthermore the present invention may be used in implants to analyze or manipulate mental or vital stats, enhance senses, feelings or stimulate organ functions. Further, the CellChip circutry may also be an essential part of nano-bots, as they provide power and control (autonomous or remote) as well as analytical components. Propulsion, actors, tools or anchor may also turn a cell-chip circuitry into a nano-bot.

Cell-chip circuitry pit may obtain nano-bot e.g. as a task force to swarm out inside organisms for specific action. The nano needle may deploy or absorb matters, molecules or particles from cells or tissues nearby. Further, the present invention allows bio-medical imaging of the inside body parts and micro field tomography.

The nano needles in the pit may further perform similar to scanning tunneling microscope (STM) with the advantage that the needle array creates 2D or 3D images of the structure of the sample. The controller of the system creates images from the measured electrical charges on the sample.

Many changes, modifications, variations and other uses and applications of the subject invention will, however, become apparent to those skilled in the art after considering this specification and the accompanying drawings, which discloses the preferred embodiments thereof. All such changes, modifications, variations and other uses and applications which do not depart from the spirit and scope of the invention are deemed to be covered by the invention, which is to be limited only by the claims which follow.

The invention claimed is:

1. A system for interacting with a cell in a living organism, further the system communicates over a communication network, the system comprising:
   a controller for releasing routing instructions, further the controller communicates through the communication network;
   a frequency generator connected to the controller for providing modulated alternating electric field with variable frequency;
   a first electrode configured to receive alternating electric field charges from the controller;
   one or more cell-chip circuitries, wherein at least one cell-chip circuitry is capacitvely coupled to the first electrode, the one or more cell-chip circuitries comprising:
   a second electrode coupled to the first electrode and configured to receive mirror alternating charges of the first electrode's alternating electric field charges;
      a harvester converts the alternating electric field into DC power and further extracts clock signals synchronized with the e-field alternating electric field frequency;
      a processor that processes external operation commands and data received from the controller;
      a pulser configured to measure alternating electric field strength of the received alternating electric field charges from the harvester and generates pulsed intervals depending upon the alternating electric field strength;
      an analog digital switch matrix configured to receive routing instructions from the controller for making conditional temporary connections under the control of the processor, further the analog digital switch matrix routes pulsed intervals;
      a bi-directional communication unit is configured to modulate commands and bi-directionally communicate data with the controller through the alternating electric e-field;
      a pit having insulated walls, wherein the pit is configured to receive the cell;
      a third electrode configured to provide a space for the pit and floats against ground, wherein the pit is formed through the space;
      an inherent artificial intelligence interpreter is configured to perform successive approximation to monitor the cell inside the pit based on receiving instructions from the controller;
      an analyzer for measuring analog values of the alternating electric e-field on the cell under the command of the inherent artificial intelligence interpreter, the analyzer communicates data to the bi-directional communication unit;
      a charge chamber for switching polarized charges into the pit to ionize the cell;
      a nano needle is configured to be inserted through the third electrode and into the pit for bi-directionally communicating the alternating electric e-field on the cell; and
      wherein, the charge chamber receives signal from the inherent artificial intelligence interpreter to determine the amount of charge potential for treatment of the cell.

2. The system according to claim 1 wherein the nano needle is movable inside the pit towards the cell.

3. The system according to claim 2 wherein the movement of nano needle inside the living organism shreds the cell.

4. The system according to claim 1, wherein the cell-chip circuitry is configured to be inserted in the living organisms to examine the cell.

5. The system according to claim 4, wherein the charge chamber is configured to ionize the cell to prevent collagen from creating fibers towards a cancer cell inside the living organism.

6. The system according to claim 1 wherein the nano needle inside the pit communicates charges on the cell surface.

7. The system according to claim 1 wherein the pit is configured to receive at least one of markers and medicines.

8. The system according to claim 1, wherein the second electrode couples capacitvely to the controller to get energy, clock, and data from mirrored alternating charges.

9. The system according to claim 1 wherein each of the one or more cell-chip circuitries are connected via charge coupling.

10. The system according to claim 1 wherein the analog value is converted to a digital value by the inherent artificial intelligence interpreter.

11. The system according to claim 1 wherein the pulsed intervals are routed to the sub-circuits of the cell-chip circuitry.

12. The system according to claim 1 wherein further comprising a plurality of nano needles configured to electronically scan electrical images of a sample, further wherein the controller creates visual images from the scanned images.

13. The system according to claim 1 wherein the nano needle projects from the pit on the command of the inherent artificial intelligence interpreter to interact with the cell.

14. The system according to claim 1, wherein a second nano needle is transferable in the living organism, wherein the second nano needle further locks in the pit when the previous nano needle is released.

* * * * *